US009901095B2

(12) United States Patent
Yang et al.

(10) Patent No.: US 9,901,095 B2
(45) Date of Patent: Feb. 27, 2018

(54) PROCESSES FOR THE PREPARATION OF PESTICIDAL COMPOUNDS

(71) Applicant: Dow AgroSciences LLC, Indianapolis, IN (US)

(72) Inventors: Qiang Yang, Zionsville, IN (US); Beth Lorsbach, Indianapolis, IN (US); Greg Whiteker, Carmel, IN (US); Gary Roth, Midland, MI (US); Carl DeAmicis, Indianapolis, IN (US); Thomas Clark, Midland, MI (US); Kaitlyn Gray, Freeland, MI (US); Yu Zhang, Carmel, IN (US); Joseck M. Muhuhi, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/485,782

(22) Filed: Apr. 12, 2017

(65) Prior Publication Data
US 2017/0215420 A1   Aug. 3, 2017

Related U.S. Application Data

(62) Division of application No. 14/829,174, filed on Aug. 18, 2015, now Pat. No. 9,661,849, which is a division of application No. 14/517,594, filed on Oct. 17, 2014, now Pat. No. 9,174,962.

(60) Provisional application No. 62/039,730, filed on Aug. 20, 2014, provisional application No. 61/892,118, filed on Oct. 17, 2013.

(51) Int. Cl.
*C07D 401/04* (2006.01)
*A01N 43/56* (2006.01)

(52) U.S. Cl.
CPC ........... *A01N 43/56* (2013.01); *C07D 401/04* (2013.01)

(58) Field of Classification Search
CPC .................................................... C07D 401/04
USPC ..................................................... 546/275.4
See application file for complete search history.

(56) References Cited

U.S. PATENT DOCUMENTS

| | | |
|---|---|---|
| 3,597,341 A | 8/1971 | Oswald |
| 4,080,457 A | 3/1978 | Harrison et al. |
| 4,260,765 A | 4/1981 | Harrison et al. |
| 4,407,803 A | 10/1983 | Haviv et al. |
| 4,536,506 A | 8/1985 | Marcoux et al. |
| 4,556,671 A | 12/1985 | Copp et al. |
| 4,734,125 A | 3/1988 | Gehring et al. |
| 4,810,719 A | 3/1989 | Appleton et al. |
| 4,824,953 A | 4/1989 | Bronn |
| 5,220,028 A | 6/1993 | Iwasawa et al. |
| 5,625,074 A | 4/1997 | Daum et al. |
| 5,631,380 A | 5/1997 | Haas et al. |
| 5,652,372 A | 7/1997 | Muller et al. |
| 5,693,657 A | 12/1997 | Lee et al. |
| 5,750,718 A | 5/1998 | Muller et al. |
| 5,817,677 A | 10/1998 | Linz et al. |
| 5,854,264 A | 12/1998 | Anthony et al. |
| 5,854,265 A | 12/1998 | Anthony et al. |
| 5,869,681 A | 2/1999 | Muller et al. |
| 6,040,331 A | 3/2000 | Yamamoto et al. |
| 6,218,418 B1 | 4/2001 | Pevarello et al. |
| 6,413,984 B1 | 7/2002 | Philippo et al. |
| 6,506,747 B1 | 1/2003 | Betageri et al. |
| 6,548,525 B2 | 4/2003 | Galemmo, Jr. et al. |
| 6,720,427 B2 | 4/2004 | Sanner et al. |
| 6,878,196 B2 | 4/2005 | Harada et al. |
| 6,916,927 B2 | 7/2005 | Bunnage et al. |
| 6,965,032 B2 | 11/2005 | Freudenberger et al. |
| 7,192,906 B2 | 3/2007 | Hirohara et al. |
| 7,196,104 B2 | 3/2007 | Askew, Jr. et al. |
| 7,319,108 B2 | 1/2008 | Scwink et al. |
| 7,774,978 B2 | 8/2010 | Ding et al. |
| 7,803,832 B2 | 9/2010 | Critcher et al. |
| 7,910,606 B2 | 3/2011 | Nazere et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,901,153 B2 | 12/2014 | Buysse et al. |
| 9,024,031 B1 | 5/2015 | Yang et al. |
| 9,029,554 B1 | 5/2015 | Yang et al. |
| 9,029,555 B1 | 5/2015 | Li et al. |
| 9,029,556 B1 | 5/2015 | Yang et al. |
| 9,044,017 B2 | 6/2015 | Yang et al. |
| 9,085,552 B1 | 7/2015 | Li et al. |
| 9,085,564 B2 | 7/2015 | Yang et al. |
| 9,102,654 B2 | 8/2015 | Yang et al. |
| 9,102,655 B2 | 8/2015 | Yang et al. |
| 9,108,932 B2 | 8/2015 | Ross et al. |
| 9,108,946 B2 | 8/2015 | Yang et al. |

(Continued)

FOREIGN PATENT DOCUMENTS

| | | |
|---|---|---|
| CN | 87107798 | 5/1988 |
| CN | 1339027 | 3/2002 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.

(Continued)

*Primary Examiner* — Patricia L Morris
(74) *Attorney, Agent, or Firm* — Carl D. Corvin; Barnes & Thornburg LLP

(57) ABSTRACT

The present application provides processes for making pesticidal compounds and compounds useful both as pesticides and in the making of pesticidal compounds.

20 Claims, No Drawings

(56) References Cited

U.S. PATENT DOCUMENTS

| | | |
|---|---|---|
| 9,115,115 B1 | 8/2015 | Yang et al. |
| 9,126,974 B2 | 8/2015 | Yang et al. |
| 9,156,813 B1 | 10/2015 | Li et al. |
| 9,174,962 B2 | 11/2015 | Yang et al. |
| 9,199,942 B2 | 12/2015 | Yang et al. |
| 9,199,964 B1 | 12/2015 | Yang et al. |
| 9,249,122 B1 | 2/2016 | Yang et al. |
| 9,255,081 B1 | 2/2016 | Li et al. |
| 9,255,082 B2 | 2/2016 | Yang et al. |
| 9,255,083 B2 | 2/2016 | Yang et al. |
| 9,260,396 B2 | 2/2016 | Yang et al. |
| 9,371,310 B2 | 6/2016 | Yang et al. |
| 9,414,594 B2 | 8/2016 | Yang et al. |
| 9,422,265 B2 | 8/2016 | Li et al. |
| 9,433,215 B2 | 9/2016 | Yang et al. |
| 9,434,712 B2 | 9/2016 | Yang et al. |
| 9,447,048 B2 | 9/2016 | Yang et al. |
| 9,522,900 B2 | 12/2016 | Yang et al. |
| 9,540,342 B2 | 1/2017 | Yang et al. |
| 9,550,751 B2 | 1/2017 | Yang et al. |
| 9,573,931 B2 | 2/2017 | Yang et al. |
| 9,580,403 B2 | 2/2017 | Li et al. |
| 9,580,405 B2 | 2/2017 | Yang et al. |
| 9,604,942 B2 | 3/2017 | Ross et al. |
| 9,611,247 B2 | 4/2017 | Yang et al. |
| 9,661,849 B2 | 5/2017 | Yang et al. |
| 9,663,489 B2 | 5/2017 | Li et al. |
| 9,670,164 B2 | 6/2017 | Yang et al. |
| 9,670,178 B2 | 6/2017 | Yang et al. |
| 2002/0013326 A1 | 1/2002 | Tiebes et al. |
| 2003/0153464 A1 | 8/2003 | Nakamura et al. |
| 2003/0213405 A1 | 11/2003 | Harada et al. |
| 2004/0043904 A1 | 3/2004 | Yamaguchi et al. |
| 2004/0082629 A1 | 4/2004 | Iwataki et al. |
| 2005/0038059 A1 | 2/2005 | Mueller et al. |
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0275592 A1 | 11/2009 | Zeng et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fußlein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0101294 A1 | 4/2012 | Hirota et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0019348 A1 | 1/2013 | Crouse et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2015/0112076 A1 | 4/2015 | Yang et al. |
| 2015/0252016 A1 | 9/2015 | Yang et al. |
| 2016/0152593 A1 | 6/2016 | Li et al. |
| 2017/0044134 A1 | 2/2017 | Yang et al. |
| 2017/0081288 A1 | 3/2017 | Yang et al. |
| 2017/0101393 A1 | 4/2017 | Li et al. |
| 2017/0215420 A1 | 8/2017 | Yang et al. |
| 2017/0217924 A1 | 8/2017 | Li et al. |
| 2017/0233367 A1 | 8/2017 | Yang et al. |

FOREIGN PATENT DOCUMENTS

| | | |
|---|---|---|
| CN | 1373662 | 10/2002 |
| CN | 1852885 A | 10/2006 |
| CN | 1307161 C | 3/2007 |
| CN | 101228134 | 7/2008 |
| EP | 0097323 | 1/1984 |
| EP | 0190457 | 8/1986 |
| EP | 0205024 | 12/1986 |
| EP | 0232538 | 8/1987 |
| EP | 0248315 | 12/1987 |
| EP | 0425948 | 5/1991 |
| EP | 0273549 | 1/1992 |
| EP | 1273582 | 1/2003 |
| EP | 1321463 | 6/2003 |
| EP | 1329160 | 7/2003 |
| EP | 1757590 A1 | 2/2007 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 1994/013644 | 6/1994 |
| WO | 1997/036897 | 10/1997 |
| WO | 1998/049166 | 11/1998 |
| WO | 2000/035919 | 6/2000 |
| WO | 2001/12189 | 2/2001 |
| WO | 2001/034127 | 5/2001 |
| WO | 2001/090078 | 11/2001 |
| WO | 2002/083111 | 10/2002 |
| WO | 2003/008405 | 1/2003 |
| WO | 2003/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2008/090382 | 7/2007 |
| WO | 2007/087427 | 8/2007 |
| WO | 2007/098826 | 9/2007 |
| WO | 2008/005457 | 1/2008 |
| WO | 2008//079277 | 7/2008 |
| WO | 2009/148858 | 12/2009 |
| WO | 2010/006713 | 1/2010 |
| WO | 2010/009290 | 1/2010 |

(56) References Cited

FOREIGN PATENT DOCUMENTS

| | | |
|---|---|---|
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045224 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2010/035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/062981 | 5/2013 |
| WO | 2013/064324 | 5/2013 |
| WO | 2013/156431 | 10/2013 |
| WO | 2013/156433 | 10/2013 |
| WO | 2013/162716 | 10/2013 |
| WO | 2015/058020 | 4/2015 |
| WO | 2015/058022 | 4/2015 |
| WO | 2015/058023 | 4/2015 |
| WO | 2015/058024 | 4/2015 |
| WO | 2015/058026 | 4/2015 |
| WO | 2015/058028 | 4/2015 |

OTHER PUBLICATIONS

Fields et al., "Preparation of Trifluoromethyl-Pyrazoles and -Pyrazolines by the Reaction of 2,2,2-Trifluorodiazoethane with Carbon-Carbon Multiple Bonds," Journal of Fluorine Chemistry, 1979, vol. 13, pp. 147-158.
Bradbury et al., "Enzyme-catalysed peptide amidation," Eur. J. Biochem. 1987, vol. 169, pp. 579-584.
International Search Report and Written Opinion for PCT/US2014/061005 dated Dec. 16, 2014.
International Search Report and Written Opinion for PCT/US2014/061006 dated Dec. 8, 2014.
International Search Report and Written Opinion for PCT/US2014/061007 dated Dec. 31, 2014.
International Search Report and Written Opinion for PCT/US2014/061009 dated Dec. 8, 2014.
International Search Report and Written Opinion for PCT/US2014/061010 dated Dec. 15, 2014.
International Search Report and Written Opinion for PCT/US2014/061012 dated Dec. 15, 2014.
International Search Report and Written Opinion for PCT/US2014/061014 dated Dec. 15, 2014.
International Search Report and Written Opinion for PCT/US2014/061016 dated Dec. 15, 2014.
International Search Report and Written Opinion for PCT/US2014/061022 dated Dec. 29, 2014.
International Search Report and Written Opinion for PCT/US2014/061023 dated Dec. 15, 2014.
International Search Report and Written Opinion for PCT/US2014/061024 dated Dec. 15, 2014.
International Search Report and Written Opinion for PCT/US2014/061027 dated Dec. 15, 2014.
International Search Report and Written Opinion for PCT/US2014/061029 dated Dec. 15, 2014.
International Search Report and Written Opinion for PCT/US2014/061030 dated Dec. 15, 2014.
International Search Report and Written Opinion for PCT/US2013/029615 dated May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Preliminary Report on Patentability for PCT/US2011/058578 dated Dec. 21, 2012.
International Search Report and Written Opinion for PCT/US2011/058578 dated Apr. 5, 2012.
Kadam, S.S. et al., "Synthesis and Tautomerism of Substituted Pyrazolo[4,3-c]pyrazoles." Eur. J. Chem., 6811-6822 (2013).
Gorelik; Zhumai Organicheskol khimi, 1980 (16), 1322, Abstract, Chemical Abstracts, Accession Number.
National Center for Biotechnology Information, PubChem Compound Database; CID=17132489,https://pubchem.ncbi.nlm.nih.gov/compound/17132489, create date Nov. 13, 2007.
Frigola; European Journal of Medicinal Chemistry 1989, 435-445.
Binz et al. "Derivatives of pyridine, etc.," CA 25:30083 (1931).

PROCESSES FOR THE PREPARATION OF PESTICIDAL COMPOUNDS

CROSS REFERENCE TO RELATED APPLICATIONS

This application is a divisional of U.S. application Ser. No. 14/829,174 filed on Aug. 18, 2015, which is a divisional of U.S. application Ser. No. 14/517,594 filed on Oct. 17, 2014, which claims the benefit of U.S. Provisional Patent Applications: Ser. No. 62/039,730, filed Aug. 20, 2014; and Ser. No. 61/892,118, filed Oct. 17, 2013, the entire disclosure of these applications are hereby expressly incorporated by reference in to this application.

TECHNICAL FIELD

This application relates to efficient and economical synthetic chemical processes for the preparation of pesticidal thioethers and pesticidal sulfoxides. Further, the present application relates to certain novel compounds necessary for their synthesis. It would be advantageous to produce pesticidal thioethers and pesticidal sulfoxides efficiently and in high yield from commercially available starting materials.

DETAILED DESCRIPTION

The following definitions apply to the terms as used throughout this specification, unless otherwise limited in specific instances.

As used herein, the term "alkyl" denotes branched or unbranched hydrocarbon chains.

Unless otherwise indicated, the term "cycloalkyl" as employed herein alone is a saturated cyclic hydrocarbon group, such as cyclopropyl, cyclobutyl, cyclopentyl, cyclohexyl.

The term "thio" as used herein as part of another group refers to a sulfur atom serving as a linker between two groups.

The term "halogen" or "halo" as used herein alone or as part of another group refers to chlorine, bromine, fluorine, and iodine.

The compounds and process of the present application are described in detail below in scheme 1.

Scheme 1

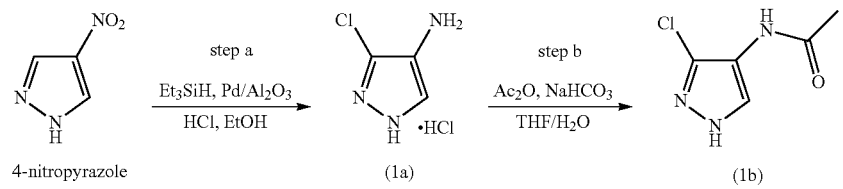

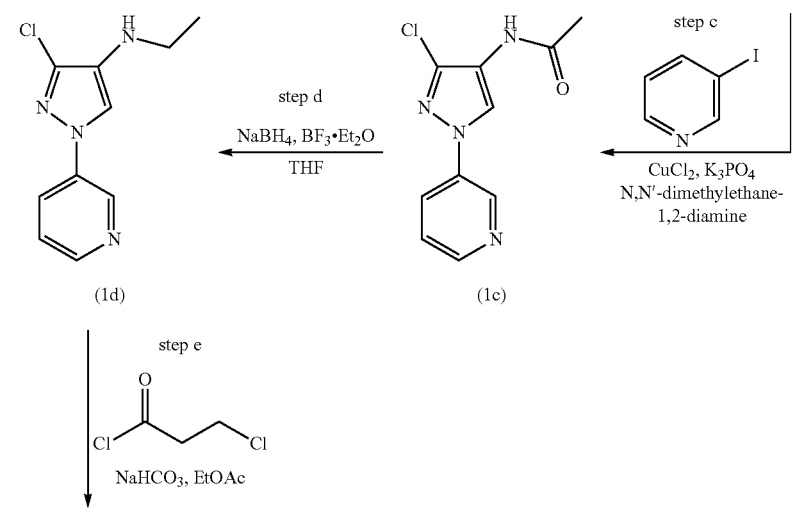

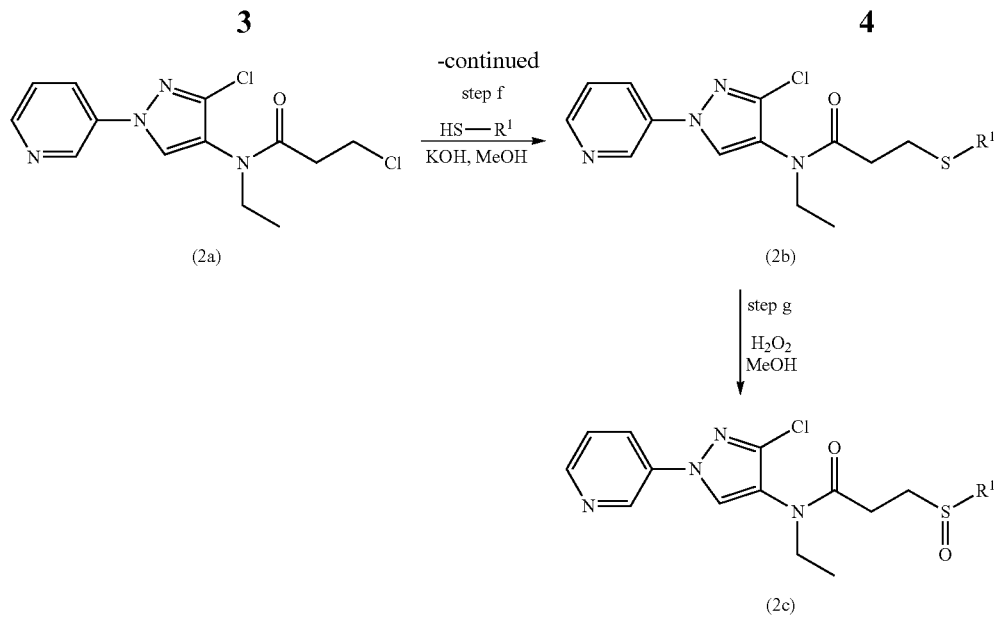

In step a of Scheme 1, 4-nitropyrazole is halogenated and reduced to yield 3-chloro-1H-pyrazol-4-amine hydrochloride (1a). The halogenation occurs at the 3-carbon through the use of concentrated (37 weight percent) hydrochloric acid (HCl). The reduction occurs with triethylsilane ($Et_3SiH$) and palladium on alumina ($Pd/Al_2O_3$, preferably about 1 to 10 weight percent palladium on alumina, more preferably about 5 weight percent). This reaction may be conducted at a temperature from about 0° C. to about 40° C., preferably from about 10° C. to about 20° C. This reaction may be conducted in a polar protic solvent, such as methanol (MeOH) or ethanol (EtOH), preferably ethanol. It was surprisingly discovered, that by utilizing about 1 equivalent to about 4 equivalents, preferably, about 2.5 equivalents to about 3.5 equivalents of triethylsilane in this step, while conducting the reaction between about 10° C. and about 20° C., gives about a 10:1 molar ratio of the desired halogenated product 3-chloro-1H-pyrazol-4-amine hydrochloride (1a)

versus the undesired product

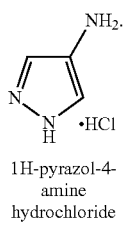

1H-pyrazol-4-amine hydrochloride

In step b of Scheme 1, 3-chloro-1H-pyrazol-4-amine hydrochloride (1a) is acylated with acetic anhydride ($Ac_2O$) in the presence a base, preferably an inorganic base, such as, sodium bicarbonate ($NaHCO_3$), at about 0° C. to about 10° C., preferably about 5° C. to yield N-(3-chloro-1H-pyrazol-4-yl)acetamide (1b). It was surprisingly discovered that a chloro substituent must be present at the 3-position for this reaction to proceed to completion and to also avoid over acylation. Described herein is a comparative example without a halogen at the 3-position that yielded the double acylated product (see "CE-1"). Further, comparative example with a bromo group at the 3-position afforded the product in a surprisingly low yield compared to the yield with the chloro group (see "CE-2").

In step c of Scheme 1, N-(3-chloro-1H-pyrazol-4-yl) acetamide (1b) is reacted with a halopyridine such as 3-bromopyridine or 3-iodopyridine in the presence of a copper salt (such as copper(I) chloride (CuCl), copper(II) chloride ($CuCl_2$), or copper(I) iodide (CuI)), potassium phosphate ($K_3PO_4$), and N,N'-dimethylethane-1,2-diamine to yield N-(3-chloro-1-(pyridin-3-yl)-1H-pyrazol-4-yl)acetamide (1c). It has been discovered that when copper(I) iodide is used that the yield of the reaction is greatly affected by the quality of the copper(I) iodide. The process may be conducted in a polar solvent, such as, acetonitrile (MeCN), dioxane, or N,N-dimethylformamide at a temperature between about 50° C. and about 110° C. It was surprisingly discovered that the addition of water during the work-up of this step maximizes the yield. Further, this synthetic method is simpler and reduces the costs of starting materials over known heteroarylation methods.

In step d of Scheme 1, N-(3-chloro-1-(pyridin-3-yl)-1H-pyrazol-4-yl)acetamide (1c) is reduced in the presence of a hydride source, preferably, sodium borohydride ($NaBH_4$) and an acid source, such as a Brønsted acid or a Lewis acid, preferably a Lewis acid, preferably borontrifluoride etherate ($BF_3Et_2O$) to yield 3-chloro-N-ethyl-1-(pyridin-3-yl)-1H-pyrazol-amine (1d). It has been surprisingly discovered that the yield of the reaction is greatly affected by the quality of the borontrifluoride etherate (purchased from different suppliers, currently, Sigma Aldrich product number 175501 being preferred).

In step e of Scheme 1, 3-chloro-N-ethyl-1-(pyridin-3-yl)-1H-pyrazol-amine (1d) is reacted with between about 1 and about 2 equivalents of 3-chloropropionyl chloride in the presence of an inorganic base, preferably, metal carbonates, metal hydroxides, metal phosphates, metal hydrides, more preferably sodium bicarbonate to yield 3-chloro-N-(3-chloro-1-(pyridin-3-yl)-1H-pyrazol-4-yl)-N-ethylpropanamide (2a).

In step f of Scheme 1, 3-chloro-N-(3-chloro-1-(pyridin-3-yl)-1H-pyrazol-4-yl)-N-ethylpropanamide (2a) is reacted with a thiol (HS-R$^1$), in the presence of an inorganic base, preferably, metal carbonates, metal hydroxides, metal phosphates, metal hydrides, more preferably, potassium hydroxide (KOH), conducted in the presence of a polar solvent, preferably methanol, wherein R$^1$ is selected from the group consisting of $C_1$-$C_4$-haloalkyl and $C_1$-$C_4$-alkyl-$C_3$-$C_6$-halocycloalkyl, preferably, R$^1$ is selected from $CH_2CH_2CF_3$ or $CH_2$(2,2-difluorocyclopropyl) to yield thioether (2b).

In step g of Scheme 1, thioether (2b) is oxidized with an oxidant, preferably hydrogen peroxide ($H_2O_2$) in a polar protic solvent to yield the desired pesticidal sulfoxides (2c). Preferred solvents are primary $C_1$-$C_4$-alcohols, especially methanol.

Alternatively, N-(3-chloro-1-(pyridin-3-yl)-1H-pyrazol-4-yl)acetamide (1c) may be prepared by the heteroarylation of N-(3-chloro-1H-pyrazol-4-yl)acetamide (1b) disclosed in Scheme 2, providing further cost savings of this process.

Scheme 2

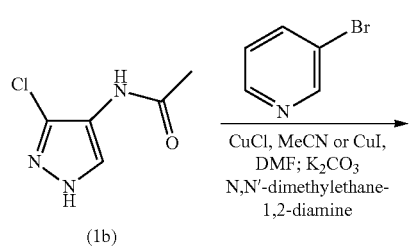

(1b)

Scheme 3

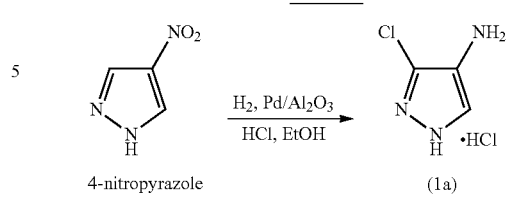

4-nitropyrazole                        (1a)

3-Chloro-N-ethyl-1-(pyridin-3-yl)-1H-pyrazol-amine (1d) may be prepared through the reaction pathway sequence disclosed in Scheme 4. In step d1, N-(3-chloro-1-(pyridin-3-yl)-1H-pyrazol-4-yl)acetamide (1c) may be alkylated with ethyl bromide (EtBr) in the presence of a base, such as sodium hydride (NaH), sodium tert-butoxide (NaOt-Bu), potassium tert-butoxide (KOt-Bu), or potassium tert-amyloxide, in a polar aprotic solvent, such as tetrahydrofuran (THF), at temperatures from about 20° C. to about 40° C., over a period of time of about 60 hours to about 168 hours, to yield N-(3-chloro-1-(pyridin-3-yl)-1H-pyrazol-4-yl)-N-ethylacetamide (1c'). It has been discovered that use of an additive, such as potassium iodide (KI) or tetrabutylammonium iodide (TBAI) decreases the time necessary for the reaction to complete to about 24 hours. It was also discovered that heating the reaction at about 50° C. to about 70° C. in a sealed reactor (to prevent loss of ethyl bromide) decreases the reaction time to about 24 hours. In step d2, N-(3-chloro-1-(pyridin-3-yl)-1H-pyrazol-4-yl)-N-ethylacetamide (1c') may be treated with hydrochloric acid in water at temperatures from about 70° C. to about 90° C., to yield 3-chloro-N-ethyl-1-(pyridin-3-yl)-1H-pyrazol-amine (1d). The reaction pathway sequence disclosed in Scheme 4 may also be performed without the isolation of N-(3-chloro-1-(pyridin-3-yl)-1H-pyrazol-4-yl)-N-ethylacetamide (1c').

Scheme 4

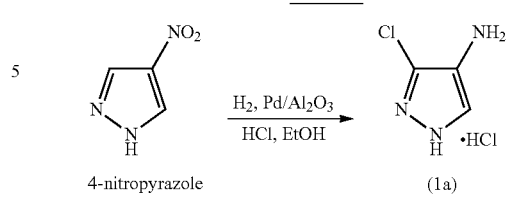

Additionally, 3-chloro-1H-pyrazol-4-amine hydrochloride (1a) may be prepared from 4-nitropyrazole. The 4-nitropyrazole is halogenated at the 3-carbon through the use of concentrated hydrochloric acid at about 0° C. to about 40° C., preferably 10° C. to about 20° C. during the reduction with palladium on alumina and hydrogen ($H_2$) to provide the described product as illustrated in Scheme 3.

EXAMPLES

The following examples are presented to better illustrate the processes of the present application.

COMPOUND EXAMPLES

Example 1: 3-Chloro-1H-pyrazol-4-amine hydrochloride (1a)

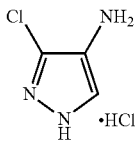

A 1000-mL, multi-neck cylindrical jacketed reactor, fitted with a mechanical stirrer, temperature probe and nitrogen ($N_2$) inlet, was charged with 4-nitropyrazole (50.0 g, 429 mmol) and palladium on alumina (5 wt %, 2.5 g). Ethanol (150 mL) was added, followed by a slow addition of concentrated hydrochloric acid (37 wt %, 180 mL). The reaction was cooled to 15° C., and triethylsilane (171 mL, 1072 mmol) was added slowly via addition funnel over 1 hour, while maintaining the internal temperature at 15° C. The reaction was stirred at 15° C. for 72 hours, after which the reaction mixture was filtered through a Celite® pad and the pad was rinsed with warm ethanol (40° C., 2×100 mL). The combined filtrates were separated and the aqueous layer (bottom layer) was concentrated to ~100 mL. Acetonitrile (200 mL) was added and the resulting suspension was concentrated to ~100 mL. Acetonitrile (200 mL) was added and the resulting suspension was concentrated to ~100 mL. Acetonitrile (200 mL) was added and the resulting suspension was stirred at 20° C. for 1 hour and filtered. The filter cake was rinsed with acetonitrile (2×100 mL) and dried under vacuum at 20° C. to afford a white solid (~10:1 mixture of 1a and 1H-pyrazol-4-amine, 65.5 g, 99%): $^1$H NMR (400 MHz, DMSO-$d_6$) δ 10.52 (bs, 3H), 8.03 (s, 1H); EIMS m/z 117 ([M]$^+$).

Example 2: N-(3-Chloro-1H-pyrazol-4-yl)acetamide (1b)

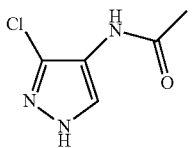

A 100-mL 3-neck round bottom flask was charged with 3-chloro-1H-pyrazol-4-amine-hydrochloride (5.00 g, 32.5 mmol) and water (25 mL). Sodium bicarbonate (10.9 g, 130 mmol) was added slowly over 10 minutes (off-gassing during addition), followed by tetrahydrofuran (25 mL). The mixture was cooled to 5° C. and acetic anhydride (3.48 g, 34.1 mmol) was added over 30 minutes while maintaining the internal temperature at <10° C. The reaction was stirred at 5° C. for 1 hour, at which point thin layer chromatography (TLC) analysis [Eluent: ethyl acetate (EtOAc)] indicated that the starting material had disappeared and a major product was exclusively formed. The reaction mixture was diluted with ethyl acetate (25 mL) and water (25 mL). The layers were separated and the aqueous layer was extracted with ethyl acetate (3×25 mL). The combined organic layers were concentrated to afford an off-white solid, which was suspended in methyl tert-butylether (MTBE, 20 mL), stirred for 1 hour, and filtered. The solid was rinsed with methyl tert-butylether (20 mL) and further dried under vacuum at room temperature (about 22° C.) for 4 hours to give a white solid (4.28 g, 83%): mp 162-164° C.; $^1$H NMR (400 MHz, DMSO-$d_6$) δ 12.90 (bs, 1H), 9.49 (s, 1H), 7.97 (s, 1H), 2.02 (s, 3H); $^{13}$C NMR (101 MHz, DMSO-$d_6$) δ 167.81, 130.07, 123.72, 116.73, 22.58; EIMS m/z 159 ([M]$^+$).

Example 3: N-(3-Chloro-1-(pyridin-3-yl)-1H-pyrazol-4-yl)acetamide (1c)

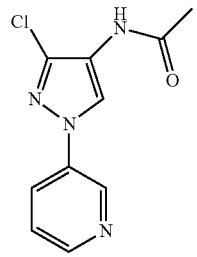 [SMILES: CC(=O)Nc1cn(-c2cccnc2)nc1Cl]

A 250 mL, 3-neck round bottom flask was charged with N-(3-chloro-1H-pyrazol-4-yl)acetamide (4.80 g, 30.1 mmol), copper(II) chloride (0.404 g, 3.01 mmol), 3-iodopyridine (7.40 g, 36.1 mmol), potassium phosphate (7.66 g, 36.1 mmol) and acetonitrile (100 mL). N,N'-Dimethylethane-1,2-diamine (1.326 g, 15.04 mmol) was added and the mixture was heated at 80° C. for 18 hours, at which point thin layer chromatography analysis [Eluent: ethyl acetate] indicated that a trace of starting material remained and a major product formed. It was filtered through a pad of Celite® and the Celite® pad rinsed with acetonitrile (50 mL). Water (300 mL) was added to the filtrates and the resulting suspension was stirred for 2 hours and filtered. The resulting solid was rinsed with water (2×20 mL) and dried under vacuum at room temperature to afford a white solid (4.6 g, 65%): mp 169-172° C.; $^1$H NMR (400 MHz, DMSO-$d_6$) δ 9.84 (s, 1H), 9.05 (dd, J=2.8, 0.8 Hz, 1H), 8.82 (s, 1H), 8.54 (dd, J=4.7, 1.4 Hz, 1H), 8.20 (ddd, J=8.4, 2.8, 1.4 Hz, 1H), 7.54, (ddd, J=8.3, 4.7, 0.8 Hz, 1H), 2.11 (s, 3H); $^{13}$C NMR (101 MHz, DMSO-$d_6$) δ 168.12, 147.46, 139.42, 135.46, 133.60, 125.47, 124.21, 122.21, 120.16, 22.62; EIMS m/z 236 ([M]$^+$).

Alternate Synthetic Route to Example 3: N-(3-Chloro-1-(pyridin-3-yl)-1H-pyrazol-4-yl)acetamide A 100-mL, 3-neck round bottom flask was charged with copper(I) chloride (59.6 mg, 0.602 mmol) and acetonitrile (10 mL), N,N'-dimethyethane-1,2-diamine (106 mg, 1.203 mmol) was added and the mixture was stirred under nitrogen to afford a solution. N-(3-Chloro-1H-pyrazol-4-yl)acetamide (480 mg, 3.01 mmol) and potassium carbonate ($K_2CO_3$, 831 mg, 6.02 mmol) were added, followed by 3-bromopyridine (570 mg, 3.61 mmol). The mixture was purged with nitrogen three times and heated at 80° C. for 18 hours. Thin layer chromatography analysis [Eluent: ethyl acetate], indicated that a trace of starting material remained and a major product formed. It was filtered through a pad of Celite® and the Celite® pad rinsed with acetonitrile (10 mL). The filtrates were concentrated to about 5 mL and water (10 mL) was added to the resulting suspension. The resulting suspension was stirred for 1 hour and filtered. The solid was rinsed with water (2×5 mL) and dried under vacuum at room temperature to afford a white solid (458 mg, 64%). Characterization matched sample prepared by previous method.

Alternate Synthetic route to Example 3: N-(3-Chloro-1-(pyridin-3-yl)-1H-pyrazol-4-yl)acetamide To a 4-neck round bottom flask was charged N,N'-dimethylformamide (DMF, 250 mL) and was degassed 2-3 times. Copper(I) iodide (17.9 g, 94.0 mmol) was added, followed by N,N'-dimethylethane-1,2-diamine (16.2 g, 188 mmol) at 25-30° C. The mixture was purged with nitrogen for 30 minutes. 3-Bromopyridine (59.4 g, 376 mmol) was added, followed by N-(3-chloro-1H-pyrazol-4-yl)acetamide (50.0 g, 313 mmol) and potassium carbonate (87.0 g, 188 mmol) at 25-30° C. The reaction mixture was purged with nitrogen for 30 minutes and heated at 95-100° C. for 3 hours, at which point HPLC analysis indicated that the reaction was complete. It was cooled to 25-30° C. and water (1 L) was added over 30-45 minutes. The resulting suspension was stirred at 25-30° C. for 30 minutes and cooled to 0-10° C. It was stirred for 12 hours at 0-10° C. and filtered. The filter cake was rinsed with water (2×250 mL) and dried to afford an off-white solid (55 g, 74%). Characterization matched sample prepared by previous method.

Example 4: 3-Chloro-N-ethyl-1-(pyridin-3-yl)-1H-pyrazol-amine (1d)

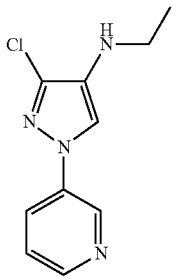

A 100 mL, 3-neck round bottom flask was charged with N-(3-chloro-1-(pyridin-3-yl)-1H-pyrazol-4-yl)acetamide (475 mg, 2.01 mmol) and tetrahydrofuran (10 mL). borontrifluoride etherate (0.63 mL, 5.02 mmol) was added and the mixture was stirred for 15 minutes to give a suspension. Sodium borohydride (228 mg, 6.02 mmol) was added and the reaction was heated at 60° C. for 4 hours, at which point thin layer chromatography analysis [Eluent: ethyl acetate, sample was prepared by treatment of reaction mixture with hydrochloric acid, followed by sodium bicarbonate basification and ethyl acetate extraction] indicated that the reaction was complete. Water (10 mL) and concentrated hydrochloric acid (1 mL) were added and the reaction was heated at 60° C. for 1 hour. The reaction mixture was cooled to room temperature and distilled to remove tetrahydrofuran. The reaction mixture was neutralized with saturated sodium bicarbonate solution to pH 8 to afford a suspension, which was stirred for 1 hour and filtered. The filter cake was rinsed with water (10 mL) and dried under vacuum to give a white solid (352 mg, 79%): mp 93-96° C.; $^1$H NMR (400 MHz, DMSO-d$_6$) δ 8.99 (d, J=2.7 Hz, 1H), 8.44 (dd, J=4.6, 1.4 Hz, 1H), 8.10 (ddd, J=8.4, 2.7, 1.4 Hz, 1H), 8.06 (s, 1H), 7.50 (dd, J=0.4, 4.7 Hz, 1H), 4.63 (t, J=6.0 Hz, 1H), 3.06-2.92 (m, 2H), 1.18 (t, J=7.1 Hz, 3H); $^{13}$C NMR (101 MHz, DMSO-d$_6$) δ 146.17, 138.31, 135.81, 132.82, 130.84, 124.10, 123.96, 112.23, 40.51, 14.28; EIMS m/z 222 ([M]$^+$).

Alternate Synthetic Route to Example 4: 3-Chloro-N-ethyl-1-(pyridin-3-yl)-1H-pyrazol-amine Step 1. N-(3-Chloro-1-(pyridin-3-yl)-1H-pyrazol-4-yl)-N-ethylacetamide (1c')

To a 3-neck, 100-mL round bottom flask was charged N-(3-chloro-1-(pyridin-3-yl)-1H-pyrazol-4-yl)acetamide (5.00 g, 21.1 mmol) and tetrahydrofuran (50 mL). Sodium tert-butoxide (3.05 g, 31.7 mmol) was added (causing a temperature rise from 22° C. to 27.9° C.), followed by ethyl bromide (4.70 mL, 63.4 mmol). The reaction was stirred at 35° C. for 168 hours, at which point HPLC analysis indicated that only 2.9% (area under the curve, AUC) starting material remained. The reaction mixture was concentrated to give a brown residue, which was diluted with ethyl acetate (50 mL) and water (50 mL). The aqueous layer was extracted with ethyl acetate (4×50 mL) and the combined organics were concentrated to give a brown residue. The residue was dissolved in dichloromethane (CH$_2$Cl$_2$, 2×10 mL) and purified by flash column chromatography using 60-100% ethyl acetate/hexanes as eluent. The fractions containing pure product were combined and concentrated to afford the title product as a yellow solid (4.20 g, 74%): mp: 87-91° C.; $^1$H NMR (400 MHz, CDCl$_3$) δ 8.98 (d, J=2.7, 0.8 Hz, 1H), 8.62 (dd, J=4.8, 1.4 Hz, 1H), 8.06 (ddd, J=8.3, 2.7, 1.4 Hz, 1H), 8.00 (s, 1H), 7.47 (dd, J=8.3, 4.7 Hz, 1H), 3.71 (q, J=7.1 Hz, 2H), 1.97 (s, 3H), 1.16 (t, J=7.2 Hz, 3H); $^{13}$C NMR (101 MHz, CDCl$_3$) δ 170.69, 148.56, 140.89, 139.95, 135.64, 126.22, 126.08, 124.86, 124.09, 43.77, 22.27, 13.15; ESIMS m/z 265 ([M+H]$^+$).

Step 1. N-(3-Chloro-1-(pyridin-3-yl)-1H-pyrazol-4-yl)-N-ethylacetamide (1c')

To a 3-neck, 100-mL round bottom flask was charged N-(3-chloro-1-(pyridin-3-yl)-1H-pyrazol-4-yl)acetamide (1.66 g, 7.0 mmol) and tetrahydrofuran (16 mL). Sodium tert-butoxide (0.843 g, 8.77 mmol, 1.25 eq) and ethyl bromide (0.78 mL, 10.52 mmol, 1.5 eq) were added and the reactor was capped with a septa. The reaction was stirred at 58° C. for 24 hours, at which point HPLC analysis indicated that only 1.97% starting material remained. The mixture was concentrated to give a brown residue, which was dissolved in water (20 mL) and ethyl acetate (20 mL). The aqueous layer was extracted with ethyl acetate (2×20 mL) and the combined organics were concentrated to dryness. The residue was passed through a silica gel plug (40 g silica) and eluted with ethyl acetate (200 mL). The filtrates were concentrated to dryness and further dried under vacuum at 20° C. to afford a yellow solid (1.68 g, 89%). Characterization matched sample prepared by previous method.

Step 1. N-(3-Chloro-1-(pyridin-3-yl)-1H-pyrazol-4-yl)-N-ethylacetamide (1c')

In a 125 mL 3-neck round-bottomed flask was added N-(3-chloro-1-(pyridin-3-yl)-1H-pyrazol-4-yl)acetamide (2.57 g, 9.44 mmol), tetrahydrofuran (55 mL), and sodium tert-butoxide (1.81 g, 18.9 mmol). The suspension was stirred for 5 minutes then ethyl bromide (1.41 mL, 18.9 mmol), and tetrabutylammonium iodide (67 mg, 0.2 mmol) were added. The resulting gray colored suspension was then heated to 38° C. The reaction was analyzed after 3 hours and found to have gone to 81% completion, after 24 hours the reaction was found to have gone to completion. The reaction mixture was allowed to cool to ambient temperature and quenched with ammonium hydroxide ($NH_4OH$)/formic acid ($HCO_2H$) buffer (10 mL). The mixture was then diluted with tetrahydrofuran (40 mL), ethyl acetate (120 mL), and saturated sodium bicarbonate (30 mL). The layers were separated and the aqueous layer was extracted with ethyl acetate (2×30 mL). The organic layers were combined and silica gel (37 g) was added. The solvent was removed in vacuo to give a solid that was purified using semi-automated silica gel chromatography (RediSep Silica 220 g column; hexanes (0.2% triethylamine)/ethyl acetate, 40/60 to 0/100 gradient elution system, flow rate 150 mL/minutes) to give, after concentration, an orange solid weighing (2.19 g, 88%).

Step 2. 3-Chloro-N-ethyl-1-(pyridin-3-yl)-1H-pyrazol-amine (1d)

A solution of N-(3-chloro-1-(pyridin-3-yl)-1H-pyrazol-4-yl)-N-ethylacetamide (1.8 g, 6.80 mmol) in hydrochloric acid (1 N, 34 mL) was heated at 80° C. for 18 hours, at which point HPLC analysis indicated that only 1.1% starting material remained. The reaction mixture was cooled to 20° C. and basified with sodium hydroxide (NaOH, 50 wt %) to pH>9. The resulting suspension was stirred at 20° C. for 2 hours and filtered. The filter cake was rinsed with water (2×5 mL), conditioned for 30 minutes, and air-dried to afford an off-white solid (1.48 g, 95%): $^1$H NMR (400 MHz, DMSO-$d_6$) δ 9.00 (dd, J=2.8, 0.8 Hz, 1H), 8.45 (dd, J=4.7, 1.4 Hz, 1H), 8.11 (ddd, J=8.4, 2.8, 1.4 Hz, 1H), 8.06 (d, J=0.6 Hz, 1H), 7.49 (ddd, J=8.4, 4.7, 0.8 Hz, 1H), 4.63 (t, J=6.0 Hz, 1H), 3.00 (qd, J=7.1, 5.8 Hz, 2H), 1.19 (t, J=7.1 Hz, 3H); $^{13}$C NMR (101 MHz, DMSO-$d_6$) δ 146.18, 138.31, 135.78, 132.82, 130.84, 124.08, 123.97, 112.23, 40.51, 14.28; ESIMS m/z 223 ([M+H]$^+$).

Alternate Synthetic Route to Example 4: 3-Chloro-N-ethyl-1-(pyridin-3-yl)-1H-pyrazol-amine To a 3-neck, 100-mL round bottom flask was charged N-(3-chloro-1-(pyridin-3-yl)-1H-pyrazol-4-yl)acetamide (5 g, 21.13 mmol) and tetrahydrofuran (50 mL). Sodium tert-butoxide (4.06 g, 42.3 mmol) was added (causing a temperature rise from 22° C. to 27.6° C.), followed by ethyl bromide (6.26 mL, 85 mmol). The reaction was stirred at 35° C. for 144 hours at which point only 3.2% (AUC) starting material remained. The reaction mixture was concentrated to give a brown residue, which was dissolved in hydrochloric acid (1 N, 106 mL, 106 mmol) and heated at 80° C. for 24 hours, at which point HPLC analysis indicated that the starting material had been consumed. The reaction was cooled to 20° C. and basified with sodium hydroxide (50 wt %) to pH>9. The resulting suspension was stirred at 20° C. for 1 hour and filtered, the filter cake was rinsed with water (25 mL) to afford a brown solid (5.18 g). The resulting crude product was dissolved in ethyl acetate and passed through a silica gel plug (50 g) using ethyl acetate (500 mL) as eluent. The filtrate was concentrated to dryness to afford a white solid (3.8 g, 80%).

Example 5: 3-Chloro-N-(3-chloro-1-(pyridin-3-yl)-1H-pyrazol-4-yl)-N-ethylpropanamide (2a)

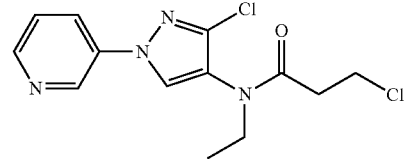 [SMILES: CCN(C(=O)CCCl)c1cn(-c2cccnc2)nc1Cl]

A 100 mL, three-neck round bottom flask was charged with 3-chloro-N-ethyl-1-(pyridin-3-yl)-1H-pyrazol-amine (2.00 g, 8.98 mmol), ethyl acetate (20 mL), sodium bicarbonate (1.89 g, 22.5 mmol) was added, followed by dropwise addition of 3-chloropropanoyl chloride (1.37 g, 10.78 mmol) at <20° C. The reaction was stirred at 10° C. for 2 hours, at which point thin layer chromatography analysis indicated that the reaction was complete [Eluent: ethyl acetate]. The reaction was diluted with water (50 mL) (off-gassing) and the layers separated. The aqueous layer was extracted with ethyl acetate (20 mL) and the combined organic layers were concentrated to dryness to afford a light brown oil which was purified by flash column chromatography using 80% ethyl acetate/hexanes as eluent. The pure fractions were concentrated to afford a white solid (1.8 g, 64%): mp 87-90° C.; $^1$H NMR (400 MHz, DMSO-$d_6$) δ 9.11 (dd, J=2.7, 0.7 Hz, 1H), 8.98 (s, 1H), 8.61 (dd, J=4.7, 1.4, 1H), 8.25 (ddd, J=8.4, 2.7, 1.4 Hz, 1H), 7.61 (ddd, J=8.3, 4.7, 0.8 Hz, 1H), 3.78 (t, J=6.3 Hz, 2H), 3.63 (q, J=7.1 Hz, 2H), 2.62 (t, J=6.2 Hz, 2H), 1.10 (t, J=7.1 Hz, 3H); $^{13}$C NMR (101 MHz, DMSO-$d_6$) δ 169.13, 148.13, 139.71, 139.12, 135.27, 129.42, 125.84, 124.24, 122.38, 43.12, 40.10, 36.28, 12.78; EIMS m/z 312 ([M]$^+$).

Example 6: N-(3-Chloro-1-(pyridin-3-yl)-1H-pyrazol-4-yl)-N-ethyl-3-((3,3,3-trifluoropropyl)thio)propanamide (Compound 6.2)

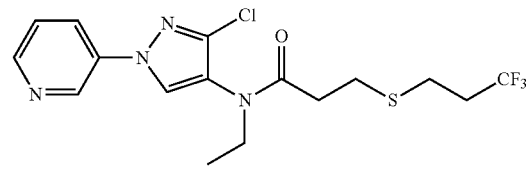 [SMILES: CCN(C(=O)CCSCCC(F)(F)F)c1cn(-c2cccnc2)nc1Cl]

A 100 mL, 3-neck round bottom flask was charged with 3-chloro-N-(3-chloro-1-(pyridin-3-yl)-1H-pyrazol-4-yl)-N-ethylpropanamide (500 mg, 1.60 mmol) and methanol (10 mL), potassium hydroxide (107 mg, 1.92 mmol) was added, followed by 3,3,3-trifluoro-propane-1-thiol (249 mg, 1.92 mmol) The mixture was heated at 50° C. for 4 hours, at which point thin layer chromatography analysis [Eluent: ethyl acetate] indicated the reaction was complete to give exclusively a new product. The reaction mixture was cooled to 20° C. and diluted with water (20 mL) and ethyl acetate (20 mL). The layers were separated and the aqueous layer was extracted with ethyl acetate (20 mL). The organics were dried over sodium sulfate ($Na_2SO_4$) and concentrated to dryness to afford a light yellow oil, which solidified upon standing to give a light yellow solid (650 mg, quantitative).

Example 7: N-(3-Chloro-1-(pyridin-3-yl)-1H-pyrazol-4-yl)-N-ethyl-3-((3,3,3-trifluoropropyl)sulfoxo)propanamide (Compound 7.2)

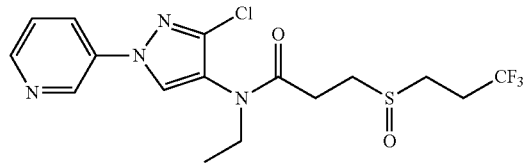 [SMILES: CCN(C(=O)CCS(=O)CCC(F)(F)F)c1cn(-c2cccnc2)nc1Cl]

N-(3-Chloro-1-(pyridin-3-yl)-1H-pyrazol-4-yl)-N-ethyl-3-((3,3,3-trifluoropropyl)thio)propanamide (57.4 g, 141 mmol) was stirred in methanol (180 mL). To the resulting solution was added hydrogen peroxide (43.2 mL, 423 mmol) dropwise using a syringe. The solution was stirred at room temperature for 6 hours, at which point LCMS analysis indicated that the starting material was consumed. The mixture was poured into dichloromethane (360 mL) and washed with aqueous sodium carbonate ($Na_2CO_3$). The organic layer was dried over sodium sulfate and concentrated to provide a thick yellow oil. The crude product was purified by flash column chromatography using 0-10% methanol/ethyl acetate as eluent and the pure fractions were combined and concentrated to afford the desired product as an oil (42.6 g, 68%): $^1$H NMR (400 MHz, DMSO-$d_6$) δ 9.09 (dd, J=2.8, 0.7 Hz, 1H), 8.98 (s, 1H), 8.60 (dd, J=4.7, 1.4 Hz, 1H), 8.24 (ddd, J=8.4, 2.7, 1.4 Hz, 1H), 7.60 (ddd, J=8.4, 4.7, 0.8 Hz, 1H), 3.61 (q, J=7.4, 7.0 Hz, 2H), 3.20-2.97 (m, 2H), 2.95-2.78 (m, 2H), 2.76-2.57 (m, 2H), 2.58-2.45 (m, 2H), 1.09 (t, J=7.1 Hz, 3H); ESIMS m/z 423 ([M+H]$^+$).

Example PE-1: Prophetic Preparation of (2,2-difluorocyclopropyl)methanethiol

To a solution of 2-(bromomethyl)-1,1-difluorocyclopropane (about 1 eq) in a solvent, such as methanol (at a concentration ranging from about 0.01 M to about 1 M), at temperatures between about 0° C. and about 40° C. may be added thioacetic acid (about 1 eq to about 2 eq), and a base, such as potassium carbonate (about 1 eq to 2 eq). An additional amount of a base, such as potassium carbonate (about 1 eq to 2 eq) may be added after a time ranging from about 30 minutes to 2 hours to the mixture to remove the acyl group. The reaction may be stirred until it is determined to be complete. The product may then be obtained using standard organic chemistry techniques for workup and purification.

Alternative preparation of (2,2-difluorocyclopropyl)methanethiol: To a solution of 2-(bromomethyl)-1,1-difluorocyclopropane (about 1 eq) in a solvent, such as methanol (at a concentration ranging from about 0.01 M to about 1 M), at temperatures between about 0° C. and about 40° C. may be added thioacetic acid (about 1 eq to about 2 eq), and a base, such as potassium carbonate (about 1 eq to 2 eq). The intermediate thioester product may then be obtained using standard organic chemistry techniques for workup and purification. To the thioester (about 1 eq) in a solvent, such as methanol (at a concentration ranging from about 0.01 M to about 1 M), at temperatures between about 0° C. and about 40° C. may be added a base, such as potassium carbonate (about 1 eq to 2 eq). The reaction may be stirred until it is determined to be complete. The product may then be obtained using standard organic chemistry techniques for workup and purification.

BIOLOGICAL EXAMPLES

Example A Bioassays on Green Peach Aphid ("GPA") (*Myzus persicae*) (MYZUPE

GPA is the most significant aphid pest of peach trees, causing decreased growth, shriveling of leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress and zucchini among other plants. GPA also attacks many ornamental crops such as carnations, chrysanthemum, flowering white cabbage, poinsettia and roses. GPA has developed resistance to many pesticides.

Several molecules disclosed herein were tested against GPA using procedures described below.

Cabbage seedling grown in 3-in pots, with 2-3 small (3-5 cm) true leaves, were used as test substrate. The seedlings were infested with 20-5-GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of the cabbage leaves until runoff. Reference plants (solvent check) were sprayed with the diluent only containing 20% by volume acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol 18 (1925), pp. 265-267) as follows.

$$\text{Corrected \% Control} = 100*(X-Y)/X$$

where
X=No. of live aphids on solvent check plants and
Y=No. of live aphids on treated plants
The results are indicated in the table entitled "Table 1: GPA (MYZUPE) and sweetpotato whitefly-crawler (BEMITA) Rating Table".

Example B Bioassays on Sweetpotato Whitefly Crawler (*Bemisia tabaci*) (BEMITA.)

The sweetpotato whitefly, *Bemisia tabaci* (Gennadius), has been recorded in the United States since the late 1800s. In 1986 in Florida, *Bemisia tabaci* became an extreme economic pest. Whiteflies usually feed on the lower surface of their host plant leaves. From the egg hatches a minute crawler stage that moves about the leaf until it inserts its microscopic, threadlike mouthparts to feed by sucking sap from the phloem. Adults and nymphs excrete honeydew (largely plant sugars from feeding on phloem), a sticky, viscous liquid in which dark sooty molds grow. Heavy infestations of adults and their progeny can cause seedling death, or reduction in vigor and yield of older plants, due simply to sap removal. The honeydew can stick cotton lint together, making it more difficult to gin and therefore reducing its value. Sooty mold grows on honeydew-covered substrates, obscuring the leaf and reducing photosynthesis, and reducing fruit quality grade. It transmitted plant-pathogenic viruses that had never affected cultivated crops and induced plant physiological disorders, such as tomato irregular ripening and squash silverleaf disorder. Whiteflies are resistant to many formerly effective insecticides.

Cotton plants grown in 3-inch pots, with 1 small (3-5 cm) true leaf, were used at test substrate. The plants were placed in a room with whitely adults. Adults were allowed to deposit eggs for 2-3 days. After a 2-3 day egg-laying period, plants were taken from the adult whitefly room. Adults were blown off leaves using a hand-held Devilbliss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in water to obtain a test solution at 200 ppm. A hand-held Devilbliss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Insecticidal activity was measured by using Abbott's correction formula (see above) and presented in Table 1.

TABLE 1

| GPA (MYZUPE) and sweetpotato whitefly-crawler (BEMITA) Rating Table | | |
|---|---|---|
| Example Compound | BEMITA | MYZUPE |
| 1a | B | B |
| 1b | B | B |
| 1c | B | B |
| 1d | B | B |
| 2a | A | A |
| Compound 6.2 | A | A |
| Compound 7.2 | A | A |

| % Control of Mortality | Rating |
|---|---|
| 80-100 | A |
| More than 0-Less than 80 | B |
| Not Tested | C |
| No activity noticed in this bioassay | D |

COMPARATIVE EXAMPLES

Example CE-1:
N-(1-Acetyl-1H-pyrazol-4-yl)acetamide

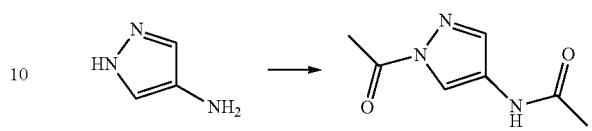

A 250-mL 3-neck flask was charged with 1H-pyrazol-4-amine (5 g, 60.2 mmol) and dichloromethane (50 mL). The resulting suspension was cooled to 5° C. and triethylamine (9.13 g, 90.0 mmol) was added, followed by acetic anhydride (7.37 g, 72.2 mmol) at <20° C. The reaction was stirred at room temperature for 18 hours, at which point thin layer chromatography [Eluent: ethyl acetate] analysis indicated that the reaction was incomplete. Additional triethylamine (4.57 g, 45.0 mmol) and acetic anhydride (3.70 g, 36.0 mmol) were added and the reaction was heated at 30° C. for an additional 3 hours to give a dark solution, at which point thin layer chromatography analysis indicated that only a trace of starting material remained. The reaction mixture was purified by flash column chromatography using ethyl acetate as eluent. The fractions containing pure product were combined and concentrated to dryness to afford an off-white solid. The solid was dried under vacuum at room temperature for 18 hours (5.55 g, 55%):
$^1$H NMR (400 MHz, DMSO-$d_6$) δ 10.30 (s, 1H), 8.39 (d, J=0.7 Hz, 1H), 7.83 (d, J=0.7 Hz, 1H), 2.60 (s, 3H), 2.03 (s, 3H); EIMS m/z 167 ([M]$^+$).

Example CE-2:
N-(3-Bromo-1H-pyrazol-4-yl)acetamide

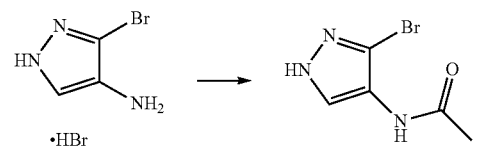

A 250 mL 3-neck round bottom flask was charged with 1H-pyraz-4-amine-hydrobromide (4.00 g, 24.7 mmol) and water (23 mL). To the mixture, sodium bicarbonate (8.30 g, 99.0 mmol) was added slowly over 10 minutes, followed by tetrahydrofuran (23 mL). The mixture was cooled to 5° C. and acetic anhydride (2.60 g, 25.4 mmol) was added over 30 minutes while maintaining the internal temperature at <10° C. The reaction mixture was stirred at ~5° C. for 20 minutes, at which point $^1$H NMR and UPLC analyses indicated that the starting material was consumed and the desired product as well as bis-acetylated byproduct were formed. The reaction was extracted with ethyl acetate and the organic layers were dried over magnesium sulfate (MgSO$_4$) and concentrated. The crude mixture was triturated with methyl tert-butylether to remove the bisacetylated product to afford ~1.24 g of a white solid. $^1$H NMR analysis showed it was 1:1.1 desired to undesired bisacetylated product. The solid was purified by flash column chromatography using 50-100% ethyl acetate/hexanes as eluent to afford the desired product as a white solid (380 mg, 7.5%) and the bisacetylated product as a white solid (~800 mg): $^1$H NMR (400 MHz, DMSO-$d_6$) δ 13.01 (s, 1H), 9.36 (s, 1H), 7.92 (s, 1H), 2.03 (s, 3H); $^{13}$C NMR (101 MHz, DMSO-$d_6$) δ 167.94, 123.93, 119.19, 119.11, 22.63; ESIMS m/z 204 ([M+H]$^+$).

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A process comprising:

(a) halogenating and reducing 4-nitropyrazole to produce

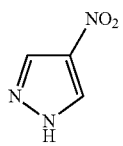

3-chloro-1H-pyrazol-4-amine hydrochloride (1a)

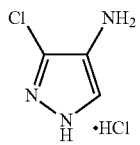
(1a)

with concentrated hydrochloric acid at a temperature between about 10° C. and about 20° C. with between about 1 and about 4 equivalents of triethylsilane and about 1 to 10 weight percent palladium on alumina;

(b) mono-acylating 3-chloro-1H-pyrazol-4-amine hydrochloride (1a) with acetic anhydride in the presence of a base to yield

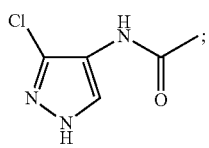
(1b)

(c) reacting 1(b) with a suitable halopyridine in the presence of a copper salt, an amine, and a base, to yield N-(3-chloro-1-(pyridin-3-yl)-1H-pyrazol-4-yl)acetamide (1c)

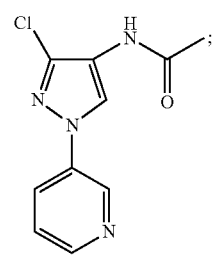
(1c)

(d) reacting 1(c) with a suitable reducing agent in the presence of an acid to yield 3-chloro-N-ethyl-1-(pyridin-3-yl)-1H-pyrazol-amine (1d)

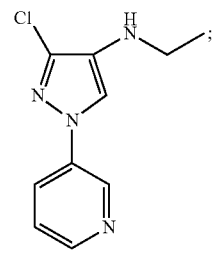
(1d)

(e) reacting (1d) with between about 1 and about 2 equivalents of 3-chloropropionyl chloride in the presence of a inorganic base to yield N-(3-chloro-1-(pyridin-3-yl)-1H-pyrazol-4-yl)-N-ethylpropanamide (2a)

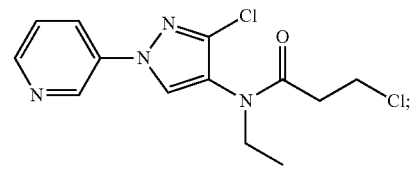
(2a)

and (f) reacting (2a) with a thiol HS-R$^1$ in the presence of a base to yield pesticidal thioethers (2b)

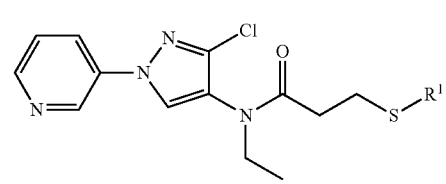
(2b)

wherein R$^1$ is selected form the group consisting of C$_1$-C$_4$ haloalkyl and C$_1$-C$_4$ alkyl-C$_3$-C$_6$ halocycloalkyl.

2. A process according to claim 1, wherein R$^1$ is C$_1$-C$_4$ haloalkyl.

3. A process according to claim 1, wherein R$^1$ is CH$_2$CH$_2$CF$_3$.

4. A process according to claim 1, wherein R$^1$ is CH$_2$(2,2-difluorocyclopropyl).

5. A process according to claim 1 further comprising oxidizing (2b) with an oxidizing agent comprising hydrogen peroxide to yield

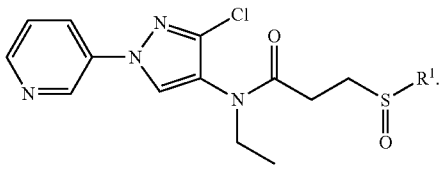

(2c)

6. The process of claim 1, wherein the base in step (b) or step (e) is sodium bicarbonate.

7. The process of claim 1, wherein step (b) is carried out at a temperature of from about 0° C. to about 10° C.

8. The process of claim 1, wherein the halopyridine in step (c) is 3-bromopyridine or 3-iodopyridine.

9. The process of claim 1, wherein the copper salt in step (c) is copper(I) chloride (CuCl), copper(II) chloride (CuCl$_2$), or copper(I) iodide (CuI).

10. The process of claim 1, wherein the copper salt in step (c) is copper(I) iodide (CuI).

11. The process of claim 1, wherein the base in step (c) is potassium phosphate (K$_3$PO$_4$).

12. The process of claim 1, wherein the amine in step (c) is N,N'-dimethylethane-1,2-diamine.

13. The process of claim 1, wherein step (c) is carried out at a temperature of from about 50° C. to about 110° C.

14. The process of claim 1, wherein step (c) is carried out in the presence of a polar solvent.

15. The process of claim 2, wherein the polar solvent in step (c) is acetonitrile (MeCN), dioxane, or N,N-dimethylformamide.

16. The process of claim 1, wherein the reducing agent in step (d) is a hydride source.

17. The process of claim 16, wherein the hydride source in step (d) is sodium borohydride (NaBH$_4$).

18. The process of claim 1, wherein the acid in step (d) is a Lewis acid.

19. The process of claim 18, wherein the Lewis acid in step (d) is borontrifluoride etherate (BF$_3$.Et$_2$O).

20. The process of claim 1, wherein the base in step (f) is potassium hydroxide (KOH).

* * * * *